United States Patent [19]

Jessel, Jr. et al.

[11] Plant 4,128

[45] Oct. 18, 1977

[54] CHRYSANTHEMUM PLANT

[75] Inventors: Walter H. Jessel, Jr., Doylestown; William E. Duffett, Akron, both of Ohio

[73] Assignee: Yoder Brothers, Inc., Barberton, Ohio

[21] Appl. No.: 715,233

[22] Filed: Aug. 18, 1976

[51] Int. Cl.[2] ..... A01H 5/00

[52] U.S. Cl. ..... Plt./74

[58] Field of Search ..... Plt./74

*Primary Examiner*—Robert E. Bagwill
*Attorney, Agent, or Firm*—Donald D. Jeffery

[57] ABSTRACT

This novel chrysanthemum originated as an induced mutation of Fiesta, and is distinguished therefrom by its medium-yellow blossoms.

1 Drawing Figure

The present invention comprises a new and distinct cultivar of *Chrysanthemum morifolium,* Ramat., hereinafter referred to by the cultivar name Festoon (No. 70318G06).

Festoon is a product of a planned sport induction program which had the objective of expanding the color range of the parental cultivar, Fiesta (No. 70318006; U.S. Plant Pat. No. 3,632). Fiesta was a product of a planned breeding program which had the objective of creating new cultivars with yellow inflorescence color, daisy type inflorens, uniform eight week response, and the ability to produce commercially acceptable quality in year round pot mum programs.

Festoon was discovered and selected by William E. Duffett and Walter H. Jessel, Jr. on Apr. 2, 1975 as one plant within a flowering block of Fiesta in a controlled environment in Barberton, Ohio. Plants within the flowering block were derived from stock plants which had been irradiated as rooted cuttings with an x-ray source of 1800 r units.

Fiesta was originated by the present inventors in 1969 as a product of a controlled breeding program. The female, or seed parent, was Cloudbank (No. 57032003; unpatented; commercially available), a white anenome originated by the present inventors from a cross between No. 55246017 (unnamed seedling) and No. 541721-1 (unnamed seedling).

The male, or pollen parent of Fiesta, was Bonnie Jean (No. 21580E01; unpatented; commercially available), a white daisy of parentage unknown to the present inventors.

The first act of asexual reproduction of Festoon was accomplished when vegetative cuttings were taken from the initial selection in July, 1975 in a controlled environment in Barberton, Ohio by a technician working under formulations established and supervised by Walter H. Jessel, Jr. and William E. Duffett. Horticultural examination of selected units initiated Apr. 2, 1976 has demonstrated that the combination of characteristics as herein disclosed for Festoon are firmly fixed and are retained through successive generations of asexual reproduction.

Festoon has not been observed under all possible environmental conditions. The phenotype may vary significantly with variations in environment such as temperature, light intensity, and daylength. The following observations, measurements, and comparisons describe plants grown in Barberton, Ohio under greenhouse environmental conditions which approximate those generally used in commercial practice, as described in Chart A which appears at the end of the present specification. A light intensity chart of general use is shown in ASHAE Trans., Vol. 64, page 64, and reference is made thereto.

The following traits have been repeatedly observed and are determined to be basic characteristics of Festoon which in combination distinguish this chrysanthemum as a new and distinct cultivar:

1. Daisy inflorescence type.
2. Flat inflorescence form.
3. Medium yellow inflorescence color with minimum color oxidation.
4. Diameter across face of inflorescence from 70 to 85 mm. at maturity.
5. Uniform eight week flowering response to photoperiodic short-day control.
6. Tall plant height (requiring one to two long day weeks prior to short days and one application of 2500 ppm. B-9 SP 14 to 21 days after the beginning of short days to obtain a flowered plant height of 30 to 45 cm.)
7. Semi-spreading branching pattern.

The accompanying color photographic drawing shows typical inflorescence and foliage characteristics of Festoon. Color representations are as nearly true as possible with illustrations of this type.

Of the many commercial cultivars known to the present inventors, the most similar existing cultivar in comparison to Festoon is the parental cultivar, Fiesta. Reference is made to attached Chart B which compares certain characteristics of Fiesta with the same characteristics of Festoon. In comparison to Fiesta, Festoon has different inflorescence color. The diameter across face of inflorescence, plant height, branching pattern, flowering response period, inflorescence form, and inflorescence type of Festoon are similar to those of Fiesta.

In the following description, color references are made to The Munsell Limit Color Cascade, 1972 edition. The color values were determined between 2:00 and 2:30 P.M. on June 17, 1976 under 200 foot-candle light intensity at Barberton, Ohio.

Botanical Classification: *Chrysanthemum morifolium,* Ramat., cv. Festoon.

Inflorescence

Capitulum:

*Form.*—Flat.

*Type.*—Daisy.

CHART A

AVERAGE GREENHOUSE CHRYSANTHEMUM ENVIRONMENTS USED FOR BARBERTON, OHIO

| SEASON | TEMPERATURES USED Night | Bright Day | Cloudy Day | LIGHTING USED | BLACK CLOTH USED | SUPP $CO_2$ |
|---|---|---|---|---|---|---|
| FALL | 65° F to 56° F | 65° F to 80° F | 60° F to 75° F | 2 to 4 weeks at 3 Hours Per Night of 7–10 f.c. | To Sept. 15 on - 5:30 PM Off - 7:30 AM | From Oct. 15 300 ppm |
| WINTER | 58° F to 62° F | 65° F to 70° F | 60° F to 65° F | 2 to 5 weeks at 5 hours Per Night of 7–10 f.c. | NONE | 300 ppm |
| SPRING | 58° F to 65° F | 65° F to 80° F | 60° F to 75° F | 2 to 4 weeks at 5 Hours Per Night of 7–10 f.c. | From Mar. 15 on - 5:30 PM Off - 7:30 AM | To Apr. 15 300 ppm |
| SUMMER | 62° F to 68° F | 70° F to 90° F | 65° F to 75° F | 1 to 2 weeks at 3 Hours Per Night of 7–10 f.c. | on - 6:00 PM Off - 8:00 AM | NONE |

CHART B

COMPARISON OF FESTOON AND FIESTA

| CULTIVAR | INFLORESCENCE COLOR | DIAMETER ACROSS FACE OF INFLORESCENCE | PLANT HEIGHT | BRANCHING PATTERN | FLOWERING RESPONSE PERIOD | INFLORESCENCE FORM AND TYPE |
|---|---|---|---|---|---|---|
| Festoon | Medium Yellow | 70 to 85 mm. | Tall | Semi-spreading | 8 week | Flat Daisy |
| Fiesta | Light Yellow | 70 to 85 mm. | Tall | Semi-spreading | 8 week | Flat Daisy |

COMPARISONS MADE OF PLANTS GROWN IN A GREENHOUSE IN BARBERTON, OHIO UNDER ENVIRONMENTAL CONDITIONS AS DESCRIBED IN CHART A.

Corolla of ray florets:

*Color (abaxial).*—26-4 to 25-5.

*Color (adaxial).*—26-4 to 25-5.

Corolla of disc florets:

*Color.*—23-10 (immature) to 27-6 (mature).

Reproductive organs:

*Androecium.*—Present disc florets only.

*Gynoecium.*—Present both ray and disc florets.

PLANT

General appearance: Semi-spreading branching pattern; tall height.

Foliage:

*Color (abaxial).*—20-15 to 20-12.

*Color (adaxial).*—20-11, but more greyed.

We claim:

1. A new and distinct cultivar of *Chrysanthemum morifolium;* Ramat, known by the cultivar name Festoon and particularly characterized as to uniqueness by the combined characteristics of daisy inflorescence type; flat inflorescence form; medium yellow inflorescence color; diameter across face of inflorescence from 70 to 85 mm. at maturity; uniform eight week flowering response to photoperiodic short-day control; tall plant height; and semi-spreading branching pattern.

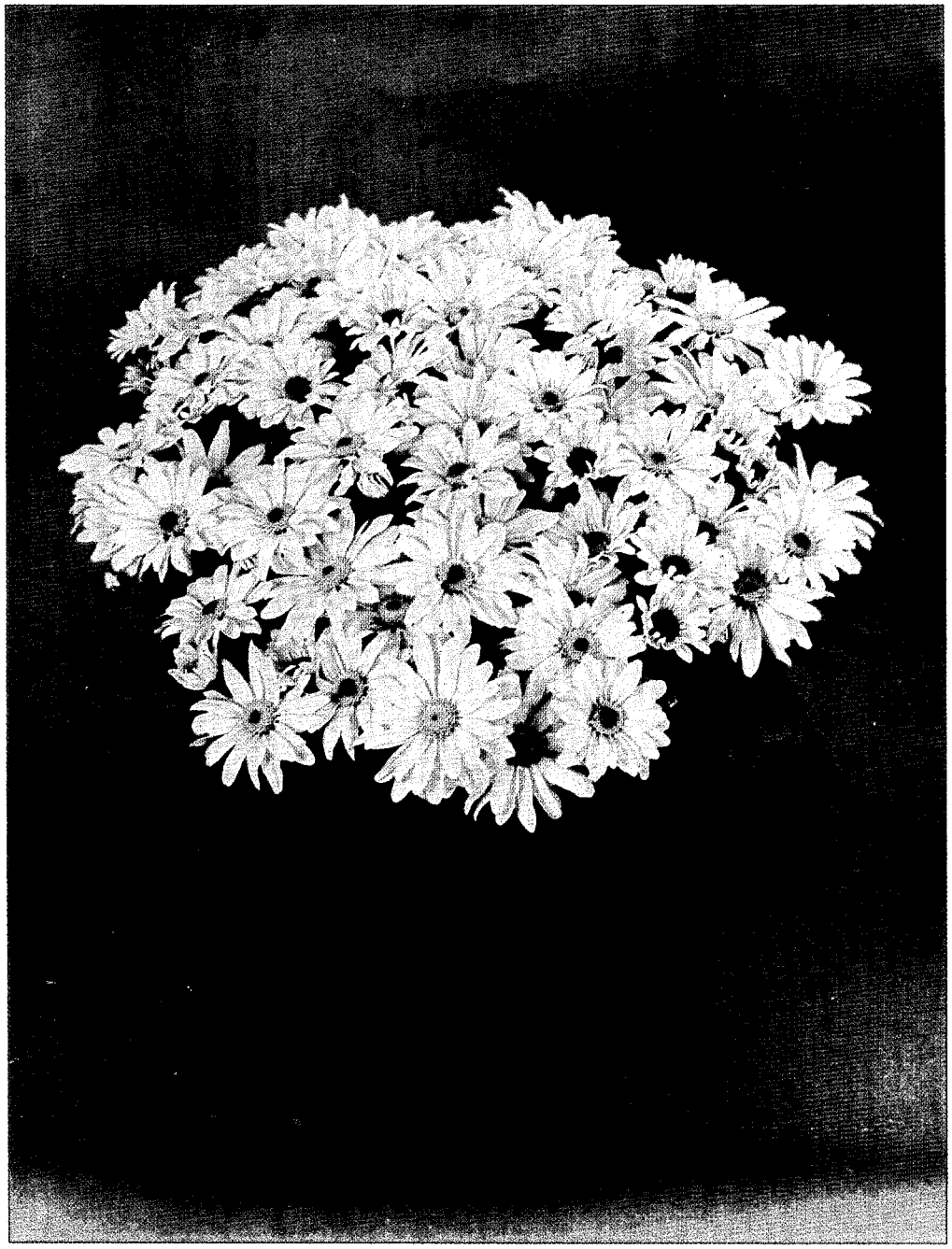

* * * * *